United States Patent [19]

Rosenfeld et al.

[11] Patent Number: 4,482,776

[45] Date of Patent: Nov. 13, 1984

[54] SEPARATION OF ORTHO AROMATIC ISOMERS BY SELECTIVE ADSORPTION WITH AN ALUMINOPHOSPHATE

[75] Inventors: Daniel D. Rosenfeld, Houston, Tex.; Denise M. Barthomeuf, Cranford, N.J.

[73] Assignee: Exxon Research & Engineering Co., Florham Park, N.J.

[21] Appl. No.: 507,761

[22] Filed: Jun. 27, 1983

[51] Int. Cl.$^3$ ................................................ C07C 7/13
[52] U.S. Cl. .............................. 585/828; 208/310 R; 502/208
[58] Field of Search ............................. 585/828, 827; 208/310 R; 502/208

[56] References Cited

U.S. PATENT DOCUMENTS

| | | | |
|---|---|---|---|
| 4,310,440 | 1/1982 | Wilson et al. | 252/435 |
| 4,313,015 | 1/1982 | Broughton | 208/310 |
| 4,376,226 | 3/1983 | Rosenfeld et al. | 585/828 |
| 4,381,419 | 4/1983 | Wylie | 585/828 |

OTHER PUBLICATIONS

Haggin, J., "Aluminophosphates Broaden Shape Selective Catalyst Types", 6/20/83, C&EN, pp. 36, 37.
Wilson, S., "Aluminophosphate Molecular Sieves: A New Class of Microporous Crystalline Inorganic Solids", pp. 1146, 1147, J. American Chem. Soc., 1982, 104.

Primary Examiner—Delbert E. Gantz
Assistant Examiner—Anthony McFarlane
Attorney, Agent, or Firm—Mitchell D. Bittman

[57] ABSTRACT

An improved process for separating ortho aromatic isomers from a feed stream containing a mixture of aromatics by contacting the feed stream with a bed of the crystalline aluminophosphate adsorbent AlPO$_4$-5. The adsorbed ortho aromatic isomers is removed from the adsorbent by desorption.

14 Claims, No Drawings

SEPARATION OF ORTHO AROMATIC ISOMERS BY SELECTIVE ADSORPTION WITH AN ALUMINOPHOSPHATE

BACKGROUND OF THE INVENTION

The field of art to which the claimed invention pertains is hydrocarbon separation. More specifically, the claimed invention relates to the separation of ortho aromatic isomers from a hydrocarbon feed stream containing a mixture of aromatics by use of a specific crystalline aluminophosphate adsorbent which selectively removes the ortho aromatic isomer from the feed stream. The selectively adsorbed ortho aromatic isomer is removed from the adsorbent through desorption.

DESCRIPTION OF THE PRIOR ART

It is known in the separation art that certain adsorbents generally comprising crystalline aluminosilicates can be utilized to separate certain hydrocarbons from mixtures thereof. In aromatic hydrocarbon separation and in particular the separation of $C_8$ aromatic isomers, it is generally recognized that certain crystalline aluminosilicates containing selected cations at the zeolitic cationic sites enhances selectivity of the zeolite for a given $C_8$ aromatic isomer. This manner of separation is particularly useful when the components to be separated have similar physical properties, such as freezing and boiling points, molecular weight and size.

The use of aluminosilicates as molecular sieves for separating aromatic isomers is common in the art. A number of processes describing the separation of para-xylene from a mixture of at least one other xylene isomer utilizing a crystalline aluminosilicate adsorbent, are shown in U.S. Pat. Nos. 3,558,730, 3,558,732, 3,626,020, and 3,663,638. Other processes which describe the adsorption separation of ethylbenzene from a mixture of xylene isomers utilizing a crystalline alluminosilicate adsorbent are shown in U.S. Pat. Nos. 3,943,182, 3,997,619, 3,998,901, and 4,021,499. However, while the separation of para-xylene and ethylbenzene from a feed stream mixture is known in the art, the separation of ortho-xylene from a feed stream mixture with meta-xylene is not common in the art. Recently issued U.S. Pat. No. 4,376,226 describes a process using the aluminosilicate adsorbent CSZ-1 to separate ortho-aromatic isomers.

The use of a novel class of crystalline aluminophosphates as molecular sieves is a recent development. U.S. Pat. No. 4,310,440 describes the aluminophosphate compositions and discloses pore dimensions of from 3A to about 10A capable of making size selective separations of molecular species. While the general use of aluminophosphates as molecular sieves is disclosed, the use of a specific aluminophosphate to separate aromatic isomers, specifically ortho aromatic isomers is unknown in the art.

Ortho aromatic isomers, such as ortho-xylene, are used commercially as precursors for producing phthalate plasticizers but the availability of the ortho aromatic isomers is restricted due to the limited ability to effectively separate the ortho aromatic isomers from a mixture of aromatics, such as a mixture of $C_8$ aromatics which include at least one of para-xylene, meta-xylene, and ethylbenzene in addition to ortho-xylene.

SUMMARY OF THE INVENTION

In brief, the invention comprises an adsorptive separation process for the separation of the ortho aromatic isomers from a hydrocarbon feed stream containing a mixture of aromatics by contacting the hydrocarbon feed stream with a bed of the crystalline aluminophosphate adsorbent AlPO$_4$-5. A raffinate stream is withdrawn from the bed, this stream containing less of the selectively adsorbed ortho aromatic isomer. The adsorbed ortho aromatic isomer on the bed is desorbed to effect displacement of the ortho aromatic isomer, and an extract stream is withdrawn from the adsorbent bed containing the ortho aromatic isomer.

DETAILED DESCRIPTION OF THE INVENTION

Hydrocarbon feed streams which can be utilized in the process of this invention contain mixtures of aromatics and an ortho aromatic isomer. This generally involves a $C_8$, $C_9$, or $C_{10}$ aromatic feed stream, with the preferred feed stream being $C_8$ aromatics containing ortho-xylene and at least one of para-xylene, meta-xylene, and ethylbenzene. Ortho aromatic isomers are defined as aromatics rings which contain at least one substituent group adjacent to another substituent group in the ring, i.e., having at least one group which has an ortho position relative to one other group of the aromatic ring. For $C_8$ aromatics it is ortho-xylene, while in the case of the $C_9$ aromatic isomer trimethylbenzene, it is pseudocumene and hemimellitene and for the $C_9$ aromatic isomer ethyltoluene it is orthoethyltoluene. Mixtures containing substantial quantities of ortho aromatic isomers and other aromatics are produced in general refinery processing and by reforming and isomerization processes, processes which are well known to the refining and petrochemical arts.

The hydrocarbon feed stream is then contacted with a bed of crystalline aluminophosphate adsorbent, entitled AlPO$_4$-5. This species of aluminophosphate, AlPO$_4$-5, is fully identified and described in U.S. Pat. No. 4,310,440 by Wilson et al., issued Jan. 12, 1982, the disclosure being fully incorporated herein by reference. The species AlPO$_4$-5 is a crystalline aluminophosphate whose essential framework structure preferably has a chemical composition, expressed in terms of molar ratios of oxides, of Al$_2$O$_3$:1.0±0.2 P$_2$O$_5$. The species AlPO$_4$-5 has a characteristic X-ray powder diffraction pattern which contains at least the d-spacings set forth in Table 2, more specifically Table 3, of U.S. Pat. No. 4,310,440. While the adsorbent is fully described in this patent, it has been surprisingly found that this adsorbent is ortho selective in a feed stream containing a mixture of aromatics, particularly aromatic isomers.

In order to obtain the adsorptive selectivity it is important to remove the organic template used in the synthesis of the AlPO$_4$-5, preferably by calcination. Generally, the AlPO$_4$-5 is calcined at 400°–600° C. for a time effective to remove the organic template, preferably at a temperature of 500° to 600° C. in air or oxygen for at least 1 hour. It is also desirable to remove any other constituents, such as water, to increase the selectivity and capacity of the adsorbent.

The AlPO$_4$-5 adsorbent can be combined with a binder, such as natural or synthetic clays (e.g. Kaolin), inorganic oxides, and lubricants and can be in any form acceptable to the separation process such as extrudates, spheres, granules or tablets.

Certain characteristics of adsorbents are highly desirable to the successful operation of a selective adsorption process. Among such characteristics are: adsorptive capacity for some weight of the ortho aromatic per weight of adsorbent; and the selective adsorption of the ortho aromatic isomer with respect to a raffinate component and the desorbent material.

Capacity of the adsorbent for adsorbing a specific volume of ortho aromatic isomer is needed for a commercially viable adsorptive separation process. Furthermore, the higher the adsorbent's capacity for the ortho aromatic isomer, the better is the adsorbent. Increased capacity of a particular adsorbent makes it possible to reduce the amount of adsorbent needed to separate the ortho aromatic isomer contained in particular charge rate of feed mixture. A reduction in the amount of adsorbent required for a specific adsorptive separation reduces the cost of the separation process. It is important that the initial capacity of the adsorbent be maintained during actual use in the separation process over some economically desirable life. Generally, the adsorbent of this invention has a capacity of at least 4% of $C_8$ aromatics by weight of adsorbent.

The second necessary adsorbent characteristic is the ability of the adsorbent to separate components of the feed; or, in other words, that the adsorbent possess adsorptive selectivity, $(\alpha)$, for one component as compared to another component. Relative selectivity can be expressed not only for one feed component as compared to another but can also be expressed between any feed mixture component and the desorbent material. The separation factor, $(\alpha)$, as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (\alpha) = \frac{[\text{weight } C/\text{weight } D]_A}{[\text{weight } C/\text{weight } D]_U} \quad \text{EQUATION 1}$$

where C and D are two components of the feed represented by weight and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or nonadsorbed) to about the same degree with respect to each other. As the $(\alpha)$ becomes less than or greater than 1.0 there is preferential adsorption by the adsorbent for one component with respect to the other. When comparing the selectivity by the adsorbent of one component C over component D, an $(\alpha)$ larger than 1.0 indicates preferential adsorption of component C within the adsorbent. An $(\alpha)$ less than 1.0 would indicate that component D is preferentially adsorbed leaving an unadsorbed phase richer in component C and an adsorbed phase richer in component D. The adsorbent of this invention in the absence of desorbent generally has an $(\alpha)$ separation factor of at least 1.5, preferably at least 2.5 of the ortho aromatic isomer (component C) over at least one of the other components (component D) of the hydrocarbon feedstream.

In order to test the AlPO$_4$-5 adsorbent with a particular feed mixture to measure the characteristics of adsorptive capacity and selectivity, a static testing procedure was employed. The procedure consisted of contacting a known weight of adsorbent with a known weight of mixed hydrocarbon feed stream. After allowing this mixture to reach equilibrium, a sample was removed and analyzed by gas chromatography. The amount of isomers in the raffinate were measured and the amount of isomers adsorbed were obtained by difference from the standard feed stream.

In a separation process, the hydrocarbon feed stream is contacted with the bed of adsorbent and a raffinate stream is withdrawn from the adsorbent bed, this stream containing less of the selectively adsorbed ortho aromatic isomer of the feed stream. The adsorbed aromatic isomers on the bed is desorbed to effect displacement thereof. The separation can be carried out in a batch or continuous process depending upon the particular process configuration used, with this invention being fully applicable to both.

The desorbing step which can be used in the various processing schemes employing this adsorbent will vary depending on the type of operation employed. The term "desorbent material" as used herein shall mean any fluid substance capable of removing a selectively adsorbed ortho aromatic isomer from the adsorbent. In the swing-bed system in which the selectively adsorbed ortho aromatic isomer is removed from the adsorbent by a purge stream, desorbent materials comprising gaseous hydrocarbons such as methane, ethane, etc., or other types of gasses such as carbon dioxide, steam, nitrogen, or hydrogen may be used at elevated temperatures or reduced pressures or both to effectively purge the adsorbed ortho aromatic isomer from the adsorbent.

However, in an adsorptive separation process which employs the adsorbent and which may be operated at substantially constant pressures and temperatures to insure a liquid phase, the desorbent material relied upon must be judiciously selected to satisfy several criteria. First, the desorbent material must displace the ortho aromatic isomer from the adsorbent with reasonable mass flow rates without itself being so strongly adsorbed as to unduly prevent the ortho aromatic isomer from displacing the desorbent material in a following adsorption cycle. Expressed in terms of the selectivity, it is preferred that the adsorbent be more selective for the ortho aromatic isomers with respect to a raffinate (e.g. other isomers), than it is for the desorbent material with respect to a raffinate. Secondly, desorbent materials must be compatible with the particular adsorbent and the particular feed stream. More specifically they must not reduce or destroy the critical selectivity of the adsorbent for the ortho aromatic isomers with respect to the raffinate. A desorbent material generally should have an $(\alpha)$ separation factor of between about 0.1 and 10, preferably between 0.2 and 5, with respect to all extract components.

Desorbent materials to be used in the process of this invention should additionally be substances which are easily separable from the feed stream that is passed into the process. After desorbing the ortho aromatic isomer of the feed, both desorbent material and the ortho aromatic isomers are removed in a mixture from the adsorbent. Without a method of separating the desorbent material, such as distillation, the purity of either the ortho aromatic isomer or the raffinate component would not be very high. It is therefore contemplated that any desorbent material used in this process will have a substantially different average boiling point than that of the feed stream. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture.

In a liquid-phase operation of the process of our invention, the desorbent materials can be an aromatic hydrocarbons such as benzene and alkylbenzenes or can be halogenated hydrocarbons. Generally, the desorbents can contain a diluent such as paraffins. For example, typical concentrations of toluene in such mixtures can be from a few volume percent up to 100 volume percent of the total desorbent material mixture but such concentrations preferably will be within the range of from about 50 volume percent to about 100 volume percent of the mixture. Other desorbents include trimethylbenzene, diethylbenzene, ethyltoluene, etc. and mixtures thereof.

Following desorption, the extract stream containing the ortho aromatic isomer is withdrawn from the adsorbent bed. Depending on the separation factor ($\alpha$) this withdrawn extract can contain relatively pure fractions of ortho aromatic isomer. However, it will be appreciated that the selectively adsorbed component is never completely adsorbed by the adsorbent, nor is the raffinate component completely non-adsorbed by the adsorbent.

In general, this adsorptive-separation process can be carried in the vapor or liquid phase, while the liquid phase is preferable. Adsorption conditions for the process of this invention may include temperatures within the range of from about ambient to about 450° F. (235° C.) and will include pressures in the range from about atmospheric to about 500 psig. Desorption conditions for the process of the invention shall generally include the same range of temperatures and pressures as described for the adsorption operation. The desorption of the selectively adsorbed ortho aromatic isomer could also be effected at subatmospheric pressures or elevated temperatures or both, or by vacuum purging of the adsorbent to remove the adsorbed isomer, but this process is not primarily directed to these desorption methods.

EXAMPLE 1

A $C_8$ aromatic feed stream (liquid phase) was added at ambient temperatures to two samples (A and B) of the crystalline aluminophosphate adsorbent AlPO$_4$-5, which were calcined for one hour at 500° C. The $C_8$ aromatic feed stream contained 1% of ethylbenzene, 1% of para-xylene, 1% of ortho-xylene, 2% meta-xylene, 2% of n-nonane and 93% of n-hexane, all by weight. After allowing this mixture to reach equilibrium, the mixture was allowed to settle and a sample was removed and analyzed by gas chromatography. The amount of $C_8$ isomers in the raffinate were measured and the amount of isomers adsorbed were obtained by difference from the standard feed stream. The capacity and the ($\alpha$) separation factor were calculated for ortho-xylene (OX) versus each of meta-xylene (MX), ethylbenzene (EB), and para-xylene (PX), as follows:

|  | Capacity Gms C$_8$ adsorbed Gms adsorbed | "$\alpha$" Separation Factor | | | | |
|---|---|---|---|---|---|---|
|  |  | OX/MX | OX/EB | OX/PX | EB/PX | PX/MX |
| AlPO$_4$-5 (A) | 0.069 | 3.3 | 3.3 | 3.2 | 1.0 0.99 | 1.0 |
| (B) | 0.057 | 2.7 | 2.7 | 2.6 | 1.0 0.99 | 1.0 |

EXAMPLE II

A sample of a $C_9$ aromatic feed stream in an amount equal to the capacity of the adsorbent was added to 200 mg of the crystalline aluminophosphate adsorbent AlPO$_4$-5, which had been calcined for about 15 hours at 500° C. and dried at 550° C. in a stream of dry nitrogen. The $C_9$ aromatic feed stream contained 33.3% of pseudocumene, 33.5% of mesitylene, 33.3% hemimellitene, all percents being by weight. After agitation at room temperature to reach equilibrium a sample of gas phase was removed and analyzed by gas chromatography. From the peaks of the chromatograms the ($\alpha$) separation factors between the various components of the feed stream were measured. The capacity and the ($\alpha$) separation factor are listed in the following Table 2:

TABLE 2

| | "$\alpha$" Separation Factor | | Capacity gms C$_9$ adsorbed gms adsorbent |
|---|---|---|---|
| | Pseudocumene Mesitylene | Pseudocumene Hemi- mellitene | Hemimellitene Mesitylene | |
| AlPO$_4$-5 | 3.5 | 1.6 | 2.2 | .16 |

EXAMPLE III

A sample of a $C_9$ aromatic feed stream containing 33.3% of para ethyltoluene (P), 33.3% of meta ethyltoluene (M), 33.3% of ortho ethyltoluene (O), all percents being by weight, was added to the AlPO$_4$-5 adsorbent as in Example II. The capacity and the ($\alpha$) separation factor were calculated for the various components of the feed stream, as listed in the following Table 3:

TABLE 3

| | "α" Separation Factor | | Capacity |
| --- | --- | --- | --- |
| | $\frac{O}{P}$ | $\frac{O}{M}$ | $\frac{\text{gms } C_9 \text{ adsorbed}}{\text{gms adsorbent}}$ |
| AlPO$_4$-5 | 1.8 | 2.1 | .17 |

EXAMPLE IV

The ($\alpha$) separation factor for the C$_8$ aromatic isomers were measured in the presence of various desorbents. A sample of a C$_8$ aromatic feed stream containing a 1:1:1:1 by molar ratio of ethylbenzene (EB):para-xylene (PX):metaxylene (MX):orthoxylene (OX), with a 1:2 molar ratio of C$_8$:desorbent (Des) was added to the AlPO$_4$-5 adsorbent as in Example II. The ($\alpha$) separation factors were calculated for the various components of the feedstream for the particular desorbent, as listed in the following Table 4:

TABLE 4

| Desorbent | $\frac{OX}{MX}$ | $\frac{OX}{PX}$ | $\frac{OX}{EB}$ | $\frac{OX}{Des}$ | $\frac{MX}{Des}$ |
| --- | --- | --- | --- | --- | --- |
| None | 5 | 4.8 | 4.5 | — | — |
| Benzene | 3.6 | 3.7 | 3.5 | 1.5 | 0.4 |
| Toluene | 3.9 | 3.8 | 3.9 | 2 | 0.5 |
| p-ethyl-toluene | 4.2 | 3.0 | 2.6 | 3.6 | 0.9 |
| Prehnitene | 4.7 | 4.5 | 4.7 | 11 | 2.3 |

The capacity for C$_8$ aromatics adsorbed, without desorbent present, was 0.18.

The above examples demonstrate the effectiveness of AlPO$_4$-5 as an adsorbent for ortho aromatic isomers with or without the use of a desorbent.

What is claimed is:

1. An adsorptive separation process for separating the ortho aromatic isomers from a hydrocarbon feed stream containing a mixture of aromatics comprising:

(a) contacting said hydrocarbon feed stream with a bed of a crystalline aluminophosphate adsorbent AlPO$_4$-5;

(b) withdrawing from said bed of adsorbent a raffinate stream containing less of the selectively adsorbed ortho aromatic isomer of the feed stream;

(c) desorbing the adsorbed ortho aromatic isomer to effect displacement thereof and withdrawing from the adsorbent bed an extract stream containing the ortho aromatic isomer.

2. Process of claim 1 further characterized in that prior to the adsorptive separation process an organic template used in the synthesis of said adsorbent is removed from said adsorbent.

3. Process of claim 2 wherein the organic template is removed from said adsorbent by calcining at 500° to 600° C. for at least 1 hour.

4. Process of claim 2 wherein the adsorbed aromatic components are desorbed by passing a desorbent material through said bed.

5. Process of claim 2 wherein the hydrocarbon feed stream contains a mixture of ortho-xylene and at least one of the aromatics selected from the group consisting of para-xylene, meta-xylene and ethylbenzene.

6. Process of claim 2 wherein the hydrocarbon feed stream contains a mixture of C$_9$ aromatics isomers.

7. Process of claim 2 wherein the hydrocarbon feed stream contains a mixture of C$_{10}$ aromatic isomers.

8. Process of claim 5 wherein the desorbent is selected from the group consisting of toluene, benzene, alkyl benzenes, halogenated hydrocarbons and mixtures thereof.

9. Process of claim 1 wherein the adsorbent has a framework structure with a formula in terms of mole ratios of oxides of Al$_2$O$_3$:1.0±0.2P$_2$O$_5$.

10. Process of claim 2 wherein the separation is carried out at a temperature within the range of ambient to 450° F. and a pressure within the range of atmospheric to 500 psig.

11. Process of claim 10 wherein the process is carried out in the liquid phase.

12. Process of claim 10 wherein the process is carried out in the vapor phase.

13. Process of claim 1 wherein the adsorbent is combined with a binder.

14. Process of claim 13 wherein the binder is selected from the group consisting of natural and synthetic clays and inorganic oxides.

* * * * *